(12) United States Patent
Furrer et al.

(10) Patent No.: US 7,632,964 B2
(45) Date of Patent: Dec. 15, 2009

(54) ORGANIC COMPOUNDS

(75) Inventors: Stefan Michael Furrer, Cincinnati, OH (US); Christophe C. Galopin, Cincinnati, OH (US); Justin Sperry, Cincinnati, OH (US); Xiaogen Yang, West Chester, OH (US); David Patrick Bratton, Liberty Township, OH (US)

(73) Assignee: Givaudan S.A., Vernier (CH)

( * ) Notice: Subject to any disclaimer, the term of this patent is extended or adjusted under 35 U.S.C. 154(b) by 547 days.

(21) Appl. No.: 10/559,194

(22) PCT Filed: Jun. 2, 2004

(86) PCT No.: PCT/CH2004/000331

§ 371 (c)(1),
(2), (4) Date: Dec. 2, 2005

(87) PCT Pub. No.: WO2004/108653

PCT Pub. Date: Dec. 16, 2004

(65) Prior Publication Data

US 2006/0142177 A1 Jun. 29, 2006

(30) Foreign Application Priority Data

Jun. 7, 2003 (GB) .................... 0313173.7

(51) Int. Cl.
*C07C 69/52* (2006.01)

(52) U.S. Cl. .................... 560/205; 514/506; 514/529

(58) Field of Classification Search .................... None
See application file for complete search history.

(56) References Cited

U.S. PATENT DOCUMENTS 2,164,188 A 6/1939 Groll et al.
2,500,005 A 3/1950 Norris

FOREIGN PATENT DOCUMENTS

DE 10212687 * 9/2002
GB 1279080 6/1972

OTHER PUBLICATIONS

Werkhoff et al. "Vacuum Headspace Method in Aroma Research: Flavor Chemistry of Yellow Passion Fruits", J. Agric. Food Chem. 1998, 46, 1076-1093.*
STN English Abstract of DE 10212687, Accession No. 2002:733900, Document No. 137:268210.*
B. Toulemonde, I.Noleau, Volatile constituents of lovage (Levisticum Officinale Koch.) Developments in Food Science, 1988, 18, pp. 641-657.*
Duhamel et al, β-Lithiated Enamines as Enolate Equivalents in Michael Additions to Enoates, Database Belstein, Synthesis, Aug. 1991, 649-654, Database accession No. BRN3536185, Germany.
Schajaenberg et al, XP002302164, Database Belstein, Chem. Ber. 70, 1937, p. 2387, Database accession No. BRN1703650, Germany.
Decaux et al, XP002302707, Database Belstein, C.R. Seances Acad. Sci. Ser. D, 287, 1968, p. 738, Database accession No. BRN3081010, Germany.
Decaux et al, XP002302720, Database Belstein, C.R. Seances Acad. Sci. Ser. D, 287, 1968, p. 738, Database accession No. BRN3081011, Germany.
Rogoff et al, Synthetic Attractants Screened in the Field as Lures for Chloropidae, Annals of the Entomological Society of America, vol. 66, No. 2, 1973, 262-263, United States.
Sturm, Die gezielte Reichstoffsysthese- Geruchliche Verwandtschaft der Isobutenyl—und Phenylgruppe, Parümerie und Kosmetik, vol. 55, No. 12, 1974, 351-355, Germany.
WPI Abstract Acc. No. 1995—265766, English language abstract of JP7165668 A; Publication Date: Jun. 27, 1995; Applicant: Nippon Zeon.
WPI Abstract Acc. No. 1982—71564E, English language abstract of NL8200855 A; Publication Date: Aug. 2, 1982; Applicant: Int. Flavours & Fragrances.
Schjaenberg et al., Über die Geschwindigkeit der alkalischen Verseifung einiger Pentensäureester., Chem. Ber., 70, 1937, p. 2387, Germany.
Decaux et al, C.R. Seances Acad. Sci. Ser. D, 267, 1968, p. 738, Germany.
BACIS; a databse of Perfumery/Flavour Materials, n-Hexyl 2-butenoate, 19089-92-0.

* cited by examiner

*Primary Examiner*—Peter G O'Sullivan
*Assistant Examiner*—Sudhakar Katakam
(74) *Attorney, Agent, or Firm*—Curatolo Sidoti Co., LPA; Joseph G. Curatolo; Peter R. Detorre

(57) ABSTRACT

Alkyl-2-enoic acid esters of formula

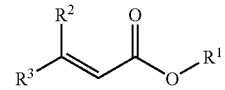

wherein $R^1$ is $C_4$, $C_5$, or $C_6$ linear or branched alkyl, e.g. n-butyl, sec-butyl, tert-butyl, n-pentyl, 3-methyl-butyl, 2-methyl-butyl, 1-methyl-butyl. 1-ethyl-propyl, 1,2-dimethyl-propyl, 2-ethylbutyl; and $R^2$ and $R^3$ are independently hydrogen, methyl or ethyl, with the proviso that a maximum of one of $R^2$ and $R^3$ is hydrogen;
with the proviso that if $R^2$ is hydrogen and $R^3$ is methyl, $R^1$ is not butyl or 1,3-dimethylbutyl, their manufacture and their use in flavor and fragrance compositions.

6 Claims, No Drawings

ORGANIC COMPOUNDS

CROSS REFERENCE TO RELATED APPLICATIONS

This application is a national stage application of International Application No. PCT/CH2004/000331, filed 2 Jun. 2004, which claims the benefit of GB 0313173.7, filed 7 Jun. 2003, from which applications priority is claimed.

This invention refers to new alkyl-2-enoic acid esters, their manufacture and their use in flavour and fragrance compositions.

The flavour and fragrance industry is always interested in new compounds that may enhance, improve, or modify the aroma or flavour in foodstuffs and consumable materials.

Surprisingly, we found certain alkyl-2-enoic acid ester compounds enhance, improve, or modify flavour notes, in particular fruity notes, e.g. blackberry and strawberry notes.

Accordingly, the present invention refers in one of its aspects to a flavour or fragrance composition comprising a compound of formula (I)

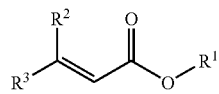

wherein $R^1$ is $C_4$, $C_5$, or $C_6$ linear or branched alkyl, e.g. n-butyl, sec-butyl, tert-butyl, n-pentyl, 3-methyl-butyl, 2-methyl-butyl, 1-methyl-butyl, 1-ethyl-propyl, 1,2-dimethyl-propyl, 2-ethylbutyl; and $R^2$ and $R^3$ are independently hydrogen, methyl or ethyl, with the proviso that a maximum of one of $R^2$ and $R^3$ is hydrogen;

with the proviso that if $R^2$ is hydrogen and $R^3$ is methyl, $R^1$ is not butyl or 1,3-dimethylbutyl.

Particularly preferred compounds for use in compositions according to the invention are butyl 3-ethylbutenoate, isobutyl 3-ethylbutenoate, pentyl 3-ethylbutenoate, 3-methylbutyl 3-methylpentenoate, 2-methylbutyl pentenoate, 2-methylbutyl 3-methylbuteonate, 2-methylbutyl 3-methylpentenoate, 2-methylbutyl 3-ethylpentenoate, 1-methylbutyl butenoate, 1-methylbutyl 3-methylpentenoate, 1-ethylpropyl 3-methylbutenoate and 1-ethylpropyl 3-methylpentenoate.

Most preferred is 2-methylbutyl 3-methylbutenoate.

Whereas some compounds of the formula (I) have been described in the literature, others have not, and are novel. Thus, the invention provides in another aspect of the invention a compound of formula (I) selected from the group of:

| chemical name | $R^1$ | $R^2$ | $R^3$ |
|---|---|---|---|
| butyl 3-ethylbutenoate | butyl | ethyl | methyl |
| butyl 3-ethylpentenoate | butyl | ethyl | ethyl |
| isobutyl 3-ethylbutenoate | isobutyl | ethyl | methyl |
| isobutyl 3-ethylpentenoate | isobutyl | ethyl | ethyl |
| sec-butyl 3-ethylpentenoate | sec-butyl | ethyl | ethyl |
| pentyl pentenoate | pentyl | ethyl | hydrogen |
| pentyl 3-ethylbutenoate | pentyl | ethyl | methyl |
| pentyl 3-ethylpentenoate | pentyl | ethyl | ethyl |
| 3-methylbutyl pentenoate | 3-methylbutyl | ethyl | hydrogen |
| 3-methylbutyl 3-methylpentenoate | 3-methylbutyl | ethyl | methyl |
| 3-methylbutyl 3-ethylpentenoate | 3-methylbutyl | ethyl | ethyl |
| 2-methylbutyl pentenoate | 2-methylbutyl | ethyl | hydrogen |
| 2-methylbutyl 3-methylbuteonate | 2-methylbutyl | methyl | methyl |
| 2-methylbutyl 3-methylpentenoate | 2-methylbutyl | ethyl | methyl |
| 2-methylbutyl 3-ethylpentenoate | 2-methylbutyl | ethyl | ethyl |
| 1-methylbutyl butenoate | 1-methylbutyl | methyl | hydrogen |
| 1-methylbutyl pentenoate | 1-methylbutyl | ethyl | hydrogen |
| 1-methylbutyl 3-methylpentenoate | 1-methylbutyl | ethyl | methyl |
| 1-methylbutyl 3-ethylpentenoate | 1-methylbutyl | ethyl | ethyl |
| 1-ethylpropyl butenoate | 1-ethylpropyl | methyl | hydrogen |
| 1-ethylpropyl pentenoate | 1-ethylpropyl | ethyl | hydrogen |
| 1-ethylpropyl 3-methylbutenoate | 1-ethylpropyl | methyl | methyl |
| 1-ethylpropyl 3-methylpentenoate | 1-ethylpropyl | ethyl | methyl |
| 1-ethylpropyl 3-ethylpentenoate | 1-ethylpropyl | ethyl | ethyl |

The compounds of formula (I) may comprise one or more chiral centres and as such may exist as a mixture of stereoisomers, or they may be resolved as isomerically pure forms. Resolving stereoisomers adds to the complexity of manufacture and purification of these compounds and so it is preferred to use the compounds as mixtures of their stereoisomers simply for economic reasons. However, if it is desired to prepare individual stereoisomers, this may be achieved according to methods known in the art, e.g. preparative HPLC and GC or by stereoselective syntheses.

In one embodiment, the compounds of formula (I) may be used in flavoured products and are useful in modifying, for example, fruity flavours. They may also be used in aromatic, herbal and spicy flavouring. Flavoured products for which the compounds of formula (I) are suitable are food and beverages such as breakfast cereals, alcoholic and non-alcoholic beverages, chewing gum, confections and frostings, fruit juices, frozen dairy desserts and mixes, fruit and water ices, gelatins, puddings, hard candy and cough drops, jams and jellies, commercial milk (whole and skim), milk products, processed fruits and fruit juices, soft candy, sweet sauces, toppings and syrups. This list of products is given by way of illustration and is not to be regarded as being in any way limiting.

The compounds of the present invention may be used in flavoured products alone or in combination with other flavour ingredients known to the person skilled in the art.

In another embodiment, the compounds of formula (I) may be used in fragrance applications, e.g. in any field of fine and functionary perfumery, such as perfumes, household products, laundry products, body care products and cosmetics.

In flavour applications, the compounds of the formula (I) may be present in consumables, e.g. a food, a beverage or a consumer healthcare product, in amounts ranging from 0.5 to 100 ppm, more preferably from 1 to 50 ppm.

When used in fragrance applications, compounds of the formula (I) can be employed in wide-ranging amounts depending upon the specific application, for example, from about 0.001 to about 10 weight percent. One application may be a fabric softener comprising about 0.001 to 0.05 weight percent of the compound. Another application may be a perfume, i.e. an alcoholic solution, comprising about 0.1 to 10 weight percent of the compound. The preferred concentrations vary between about 0.1 and 5 weight percent. However, these values should not be regarded as limiting on the present invention, since the experienced perfumer may also achieve effects with even lower concentrations or may create novel accords with even higher amounts.

Accordingly, a further aspect of the present invention refers to a method of improving, enhancing or modifying a flavoured or fragranced product comprising the step of adding thereto an olfactory acceptable amount of a compound of formula (I).

The compounds of formula (I) may be synthesised from commonly-available starting materials by acidic catalyst esterification of carboxylic acids or acid chlorides according to synthetic protocols known in the art. Examples of acidic catalyst are para-toluene sulfonic acid monohydrate, tartaric acid and $H_2SO_4$. Optically pure compounds of formula (I) and stereoisomer mixtures of a compound of formula (I) enriched in one stereoisomer may be synthesised by starting from optically pure alcohol, e.g. S-(−)-2-methylbutanol, or an stereoisomer mixture enriched in one stereoisomer alcohol respectively.

There now follows a series of non-limiting examples that illustrate the invention.

EXAMPLE 1

2-Methylbutyl 3-methylbutenoate

At room temperature under nitrogen in a 500 ml flask, a mixture of 87.3 g of 3,3-dimethylacrylic acid (0.85 mol) and 134.7 g of DL-2-methyl-1-butanol (1.50 mol, 1.75 eq.) and 4.25 g of para-toluene suflonic acid monohydrate (0.024 mol, 0.026 eq.) was treated with 100 ml heptane and then heated at reflux at 90° C. for 14 hours while 15.4 ml (0.85 mol) of $H_2O$ was collected in a Dean-Stark trap. The result was an orange solution. The solution was extracted with MTBE/brine (2×350 ml/200 ml brine). The organic layers were washed with $NaHCO_3$ (200 ml saturated solution), brine (200 ml), dried over $MgSO_4$ and concentrated. 205 g of a orange liquid was recovered, which was purified by distillation over a 30 cm plate-column. 131.1 g of a colorless liquid was recovered (bp 58° C./3.5 torr (4.7 bar) 90.5% yield).

$^1$H NMR: 5.69 (s, 1H), 3.93 (dq, 2H), 2.17 (s, 3H), 1.89 (s, 3H), 1.74 (m, 1H), 1.44 (m, 1H), 1.20 (m, 1H), 0.91 (m, 6H). $^{13}$C NMR: 116, 68, 34, 27, 26, 20, 16, 11. MS: 170 (M+), 100, 83, 70, 55, 43.

Taste description (4 ppm in water): fleshy, metallic, skinny, floral, complex, powdery, fatty.

Odour description: blackberry, peely, light tobacco with metallic aspects

EXAMPLE 2

Beverage with Blackberry Flavour 4 ppm 2-Methylbutyl 3-methylbutenoate was added to a beverage base (a) containing 0.15% by weight of the fruit flavour (b). Comparing the resulting composition with the aroma note of the starting beverage, the green, seedy and ionone notes were enhanced. The overall impression showed a nice complexing effect. By "complexing effect" is meant that the flavour profile is less simplistic, it rounds up the flavour profile.

(a) Beverage Base

|  | weight % |
|---|---|
| sugar | 10.00 |
| citric acid | 0.15 |
| water | 89.85 |

(b) Composition of a Blackberry Flavour

|  | parts by weight 1/1000 |
|---|---|
| water (deionized), | 533.2000 |
| propylene glycol | 225.0000 |
| ethyl alcohol 190 PR grain | 225.0000 |
| blackberry essence 100x | 10.0000 |
| ethyl butyrate | 2.2000 |
| ethyl pyruvate | 1.1502 |
| maltol | 1.0000 |
| raspberry ketone | 0.5000 |
| 2-heptanol | 0.4000 |
| hexanol | 0.2160 |
| 2-methyl butyric acid | 0.2133 |
| cis-3-hexenyl acetate | 0.1944 |
| acetaldehyde diethyl acetal | 0.1485 |
| methyl amyl ketone | 0.1350 |
| 4-terpinenol | 0.1134 |
| alpha-terpineol crude | 0.1080 |
| ethyl isovalerate | 0.0999 |
| ethyl caproate | 0.0999 |
| furaneol | 0.0918 |
| menthol | 0.0405 |
| hexyl acetate | 0.0378 |
| trans-2-hexenal | 0.0216 |
| ionone | 0.0108 |
| dimethyl sulfide | 0.0081 |
| menthyl acetate | 0.0054 |
| benzyl acetate | 0.0027 |
| ambrette seed absolute | 0.0027 |
| total | 1000.0000 |

EXAMPLE 3

Beverage with Strawberry Flavour 8 ppm 2-Methylbutyl 3-methylbutenoate was added to a beverage base (a) of Example 2 containing 0.20% by weight of the fruit flavour (c). Comparing the resulting composition with the aroma note of the starting beverage, seediness, fattiness and red fruit character was increased, and almost gave a raspberry note to the strawberry profile.

(c) Composition of a Strawberry Flavour

|  | parts by weight 1/1000 |
|---|---|
| 2-methylbutyl isovalerate | 5.00 |
| ethyl butyrate | 19.00 |
| ethyl isovalerate | 2.00 |
| cis-3-hexenol | 15.00 |
| furaneol 20% in propylene glycol | 100.00 |
| ethyl caproate | 0.23 |
| methyl-2-methyl butyrate | 0.22 |
| benzaldehyde | 0.40 |
| delta-dodecalactone | 0.30 |
| gamma-decalactone | 0.70 |
| diacetyl, 10% in triacetin | 0.17 |
| acetic acid | 0.03 |
| butyric acid | 0.08 |
| propylene glycol | 856.87 |
| total | 1000.00 |

We claim:

1. A flavour composition comprising 2-methylbutyl 3-methylbutenoate.

2. A flavoured product comprising an effective amount of a compound of formula (I)

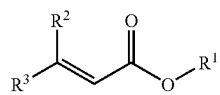

wherein R¹ is 2-methylbutyl; and R² and R³ are methyl.

3. A flavoured product according to claim 2 comprising a compound of formula (I) in an amount ranging from 0.5 ppm to 100 ppm.

4. A flavoured product according to claim 2 selected from a food, a beverage, pharmaceutical, oral hygiene product or healthcare product.

5. A method of or modifying a flavoured product comprising adding thereto an olfactory acceptable amount of 2-methylbutyl 3-methylbutenoate as defined in claim 1.

6. A compound of formula (I)

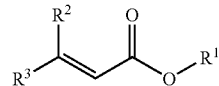

wherein R¹ is 2-methylbutyl; and, R² and R³ are methyl.

* * * * *

UNITED STATES PATENT AND TRADEMARK OFFICE
CERTIFICATE OF CORRECTION

PATENT NO. : 7,632,964 B2  Page 1 of 1
APPLICATION NO. : 10/559194
DATED : December 15, 2009
INVENTOR(S) : Furrer et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 713 days.

Signed and Sealed this

Second Day of November, 2010

David J. Kappos
*Director of the United States Patent and Trademark Office*